United States Patent [19]

Fabinski et al.

[11] Patent Number: 5,088,313
[45] Date of Patent: Feb. 18, 1992

[54] MONITORING PRESSURE INTERFERENCE IN GAS ANALYZERS

[75] Inventors: Walter Fabinski, Kriftel; Georg Taubitz, Oberursel; Gerhard Franck; Josef Nevole, both of Frankfurt, all of Fed. Rep. of Germany

[73] Assignee: Hartmann & Braun, Frankfurt am Main, Fed. Rep. of Germany

[21] Appl. No.: 443,259

[22] Filed: Nov. 29, 1989

[30] Foreign Application Priority Data

Nov. 30, 1988 [DE] Fed. Rep. of Germany ....... 3840322

[51] Int. Cl.$^5$ ............................................. G01D 18/00
[52] U.S. Cl. ..................................... 73/1 G; 73/23.21
[58] Field of Search ..................... 73/1 G, 23.21–23.29

[56] References Cited

U.S. PATENT DOCUMENTS

| 1,633,352 | 6/1927 | Tate ..................... 73/23.21 |
| 2,149,441 | 3/1937 | Jacobson ......................... 73/23.21 X |
| 3,031,882 | 5/1962 | Thayer et al. ...................... 73/23.21 |
| 3,894,433 | 7/1975 | Riester et al. ...................... 73/861.56 |
| 4,279,142 | 7/1981 | McIntyre ............................... 73/1 G |
| 4,297,871 | 11/1981 | Wright et al. ......................... 73/23.3 |
| 4,385,910 | 5/1983 | Eilers et al. ......................... 73/1 G X |
| 4,389,881 | 6/1983 | Butler et al. ......................... 73/1 G X |
| 5,003,175 | 3/1991 | Fabinski et al. ................... 73/1 G X |

FOREIGN PATENT DOCUMENTS

| 1211423 | 2/1966 | Fed. Rep. of Germany. |
| 1523019 | 7/1969 | Fed. Rep. of Germany. |
| 1498896 | 4/1970 | Fed. Rep. of Germany. |
| 1903355 | 7/1970 | Fed. Rep. of Germany. |
| 2104894 | 11/1971 | Fed. Rep. of Germany. |
| 2504275 | 10/1977 | Fed. Rep. of Germany. |
| 1000811 | 2/1983 | U.S.S.R. ............................... 73/1 G |
| 1185097 | 10/1985 | U.S.S.R. ............................... 73/1 G |
| 1385063 | 3/1988 | U.S.S.R. ............................... 73/1 G |

OTHER PUBLICATIONS

*General Handbook of Online Analyzers;* Chapter 8, pp. 106–108; D. J. Haskins; Published, Chichester 1981.

*Primary Examiner*—Tom Noland
*Attorney, Agent, or Firm*—R. H. Siegemund

[57] ABSTRACT

Apparatus for monitoring and correcting gas analyzers having a measuring chamber with an inlet and an outlet, and a pump for supplying a pressurized measuring gas, further includes a flow throttle for providing flow resistance and being connected to the outlet of the analyzer to obtain a gas pressure in the chamber above a level downstream from the throttle; a pressure transducer is connected to measuring gas pressure of the measuring gas upstream from the throttle but downstream from the pump, preferably also upstream from the analyzer; an output signal from the transducer is used for correcting errors of the measuring signal of the gas analyzer caused by variations of gas pressure in the measuring chamber on account of variations in the gas pressure, for using the same output signal to extract a rate of flow indication as to the measuring gas and for ascertaining that the flow remains within specified limits.

4 Claims, 1 Drawing Sheet

MONITORING PRESSURE INTERFERENCE IN GAS ANALYZERS

BACKGROUND OF THE INVENTION

The present invention relates to the measuring and monitoring of a stream or flow of gas; the flow being e.g. produced by a pump, for pumping a measuring gas through a measuring chamber of a gas analyzing instrument whereby in addition it is necessary to ascertain what interferences occur resulting from pressure and flow through variations as they may affect the measuring signal of that analyzer.

The gas flow in gas analyzers running and operating on a continuous basis, is usually monitored by means of devices that measure and indicate volume and/or mass flow and are in the following designated as flow quantity measuring devices. Particularly automatically operated gas analyzers but without continuous observation are advantageously equipped with and supplemented by a continuous flow measurement and by additionally monitoring limit values e.g. whether minimum flow conditions are no longer met, or maximum quantities of flow are exceeded. In other words it is monitored whether or not the gas flow remains between minimum and maximum values whereby of course in cases the limit is exceeded in one way or another certain warning signals issue permitting the taking of requisite steps to remedy the situation.

Certain gas analyzers react to variations in pressure in the measuring chamber on the basis of the specific physical principle involved in the measurement. Such pressure variations may cause an undesired modification of the measuring signals. Therefore in order to maintain the requisite accuracy of measurement it is either necessary to provide an absolute constancy of the pressure in the measuring chamber or to provide for an automatic correction that takes care of ensuing and existing pressure variations.

Simple gas measuring devices include mechanical, pneumatic measuring principles and simply measure the gas flow and monitoring the same. Here are used e.g. floating devices within a conically calibrated glass tube. The hovering height of the floating body such as a sphere indicates the amount of material that flows through, using a suitable calibration for the indication. The desired monitoring and signaling in case of a deviation is carried out on the basis of detection of maximum and minimum values. They are ascertained in that inductive, or optical magnetic transducer structures are arranged around this glass tube; when the floating body has reached a certain limit in one way or another (or both) interaction(s) result(s) in the production of a warning signal. Devices of this kind are disclosed in German printed patent application 25 04 275 and 14 98 896. Application 2,504,275 is based on an U.S. application, Ser. No. 441,997, filed 02/13/1974 and now U.S. Pat. No. 3,894,433.

Another way of monitoring limit values uses pneumatic electrical pressure sensitive switches responding to changes in static pressure of the gas analyzer. A device of this nature is for example disclosed in German printed patent application 12 11 423. Other pneumatic measuring systems use a measuring diaphragm and capillary device and respond to a differential pressure; arrangements of this kind are disclosed in German printed patent applications 15 23 019 and 19 03 353. A gas flow can also be ascertained by using in calorimetric systems and here one uses electrically heated wires which are (more or less) cooled by the (variable) gas flow. The cooling of the wire determines its resistance and any changes are ascertained by electric signal processing. Equipment of the kind is shown in German printed application 21 04 894.

In all these various methods when using an electrical output signal one uses a normal or physical indication of the flow through as well as limit monitoring under utilization of comparing adjustable desired or reference values with the actual values. Piezoelectric transducers are used often for measuring the pressure in a chamber, and the output of the transducer is used for correcting the pressure dependent influence on the measuring signal. The measuring signal output of such a transducer is thus introduced into an electrical signal processing circuit as generally pertaining to the analyzer.

The methods and equipments as described are using always at least two measuring transducers for obtaining and providing for the following three functions (i) measuring the quantity of flow through and indication of the rate of flow value; (ii) monitoring the limits of the flow through amount; and (iii) measuring the pressure in the measuring chamber for correcting the pressure dependent analyzing signal. Quite clearly this requires relatively extensive technical expenditure and is on one hand expensive and on the other hand prone to errors in its own right owing to the result in complexity.

DESCRIPTION OF THE INVENTION

It is an object of the present invention to provide a new and improved gas flow measuring device in conjunction with a gas analyzer operating under conditions in which pressure and flow dependent interferences are to be eliminated, under specific utilization of a flow resistor and pressure transducer.

In accordance with the preferred embodiment of the present invention it is suggested to provide a flow resisting, throttling device downstream from the analyzer so as to raise the pressure therein above discharge level values downstream from the throttle, a pressure transducer is connected the same to the gas flow system upstream from the throttling device but downstream from the pump. The signal in the pressure transducer represents an absolute value and is used as measuring value for ascertaining the flow through amount as well as interferences on the measuring signal to be used in a correction.

The invention is based on the following principle. In accordance with known laws underlying flow dynamics a gas flow through the measuring chamber and the respective conduits of the analyzer generally produces a pressure increase that has a functional relationship to the amount of a gas flow, on a volumetric basis, upstream from the flow resistance device. If one measures the pressure upstream from that throttling resistance and considers it as absolute value which provides concurrently geodesic height and barometric pressure variations, it is feasible to use that pressure measuring signal value and to process it to extract them from all of the three functions mentioned above, namely, rate of flow through measurement proper; limit monitoring; and correction of errors based on pressure variations. The signal processing and corrective computation is preferably carried out by means of a microprocessor as it is usually available already in modern and contemporary analyzers.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DETAILED DESCRIPTION OF THE DRAWINGS

Figure 1:
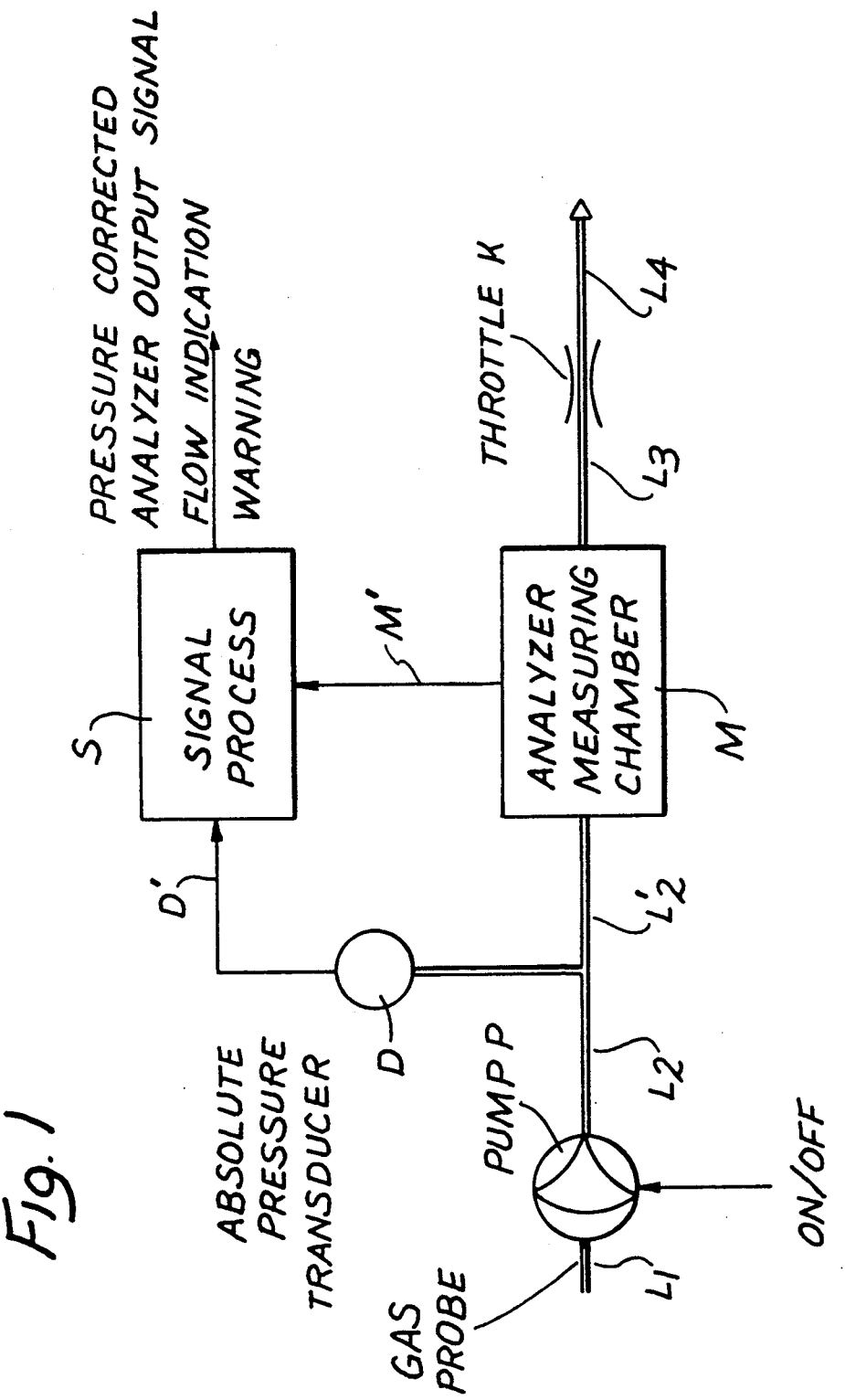
FIG. 1 shows somewhat schematically a preferred embodiment of the present invention for carrying out method under utilization of equipment in accordance with best mode considerations.

The measuring gas is assumed to enter the system through a conduit L1 or is available at the conduit and is pumped by means of a pump P into a conduit L2. A conduit or tube or pipe or hose connects the pump with a measuring chamber M of a gas analyzer of any construction. The details of the construction of the analyzer do not play any important part as far as the invention is concerned except that it is assumed that the analyzer itself does not provide for any automatic pressure compensation. It does produce an electric output (or set of outputs) fed to a signal processing stage S.

The gas flows out of the measuring chamber M into a conduit L3 leading to a throttling device and flow resistor K. The resistor K is realized through capillary construction or any other throttling device of other known construction. L4 is a conduit through which the gas leaves the system. Under steady state conditions of course the overall flow is the same. There flows enough gas into the system through L1 as it leaves through L4, and the device K therefore establishes a definite pressure relationship which as compared with the actual output pressure at the conduit L4 means that the pressure in L3, in M and in L2 is increased.

In order to obtain the requisite functions and to carry out the purpose of the invention, a pressure transducer D constructed as an absolute pressure transducer is connected to line L2; with L2' denoting that portion of line L2 which exceeds between the analyzer M and the instrument/transducer D. In other words D measures pressure in absolute sense and does not measure any pressure in line L2 in relation to or relatively to the ambient pressure. The pressure transducer D is shown upstream from chamber M and measures the pressure in the conduit L2/L'2 on an absolute scale basis. The transducer D could actually be in the measuring chamber, or even downstream thereof, but must remain upstream from flow resistor K. The downstream position of D relative to M depends on the flow resistances in the pressure line portion L'2 and on the point whether the flow resistance from M to K is negligible. The signal of the transducer D is an electrical signal passing to processing stage S of general design.

The signal from the pressure transducer D is used in stage S for offsetting and correcting pressure variations to the extent they interfere with the correctness of the analyzing measuring signal M'. The pressure variations are firstly related functionally to the flow through in accordance in accordance with the flow dynamic laws in a square relationship. Accordingly variations in flow-through are translated into pressure variations and monitored by the device D.

One can consider that the pressure signal is composed of a second component having to do and being related to the geodetic height of the place of measurement. This may be quite important where the measuring instrument is located in a mobile equipment and mountaneous regions are covered. Also in the case of calibration the elevation is an important factor.

In addition a still further constant component is the pressure as it is reflected by output equipment back into the output line L4. Here of course one may have to consider relatively slowly variable barometric pressure variations. These quasistatic pressure relations and conditions cause some interference and falsification of the measuring signal if quantity of flow is acquired through measuring absolute values. This means that the limit values in the system are subject to these quasistatic changes. In order to eliminate them it is suggested to periodically measure the static pressure in the chamber in a certain periodic time interval and to use that resulting value for correcting the flow through measurement. The correction may involve a brief shut off of the gas flow into line L1 or a brief stoppage of the pump. In the present case equipment was chosen which for example for an average flow value of 50 l/hour needs an upper limit value of 60 l/hour and the lower one of 40 l/hour. The dynamic pressure variations are about 70 mbar for a capillary throttling resistor K having 0.7 mm diameter and the length of 15 mm.

The invention is not limited to the embodiments described above but all changes and modifications thereof, not constituting departures from the spirit and scope of the invention, are intended to be included.

We claim:

1. Arrangement for monitoring and correcting a gas analyzer having a measuring chamber with an inlet and an outlet, there being pumping means for supplying a pressurized measuring gas, said gas analyzer producing a measuring signal, comprising:

a flow throttle for providing flow resistance and being connected to the outlet to obtain an absolute gas pressure in the chamber above a level downstream from the throttle;

pressure transducer means connected to the analyzer for measuring absolute gas pressure of the measuring gas upstream from the throttle but downstream from the pump; and means for using an output signal from the transducer for correcting errors of the measuring signal of the gas analyzer on account of any variations in the gas pressure in the measuring chamber, and for using the same output signal to extract a rate of flow indication as to the measuring gas.

2. Arrangement as in claim 1 and including means for interrupting the gas flow periodically so that the transducer measures static pressure and means for using this static pressure as a reference value.

3. Apparatus as in claim 1, the transducer means being upstream from the analyzer.

4. Apparatus as in claim 1, and including means to ascertain whether the flow remains within specified limits.

* * * * *